(12) United States Patent
Fojtik

(10) Patent No.: US 11,986,605 B2
(45) Date of Patent: May 21, 2024

(54) ELONGATED MEDICAL INSTRUMENTS WITH FLEXIBILITY ENHANCING FEATURES

(71) Applicant: Transit Scientific, LLC, South Salt Lake, UT (US)

(72) Inventor: Shawn P. Fojtik, Park City, UT (US)

(73) Assignee: Transit Scientific, LLC, Salt Lake City, UT (US)

( * ) Notice: Subject to any disclaimer, the term of this patent is extended or adjusted under 35 U.S.C. 154(b) by 0 days.

(21) Appl. No.: 16/261,557

(22) Filed: Jan. 29, 2019

(65) Prior Publication Data
US 2019/0232018 A1 Aug. 1, 2019

Related U.S. Application Data

(60) Provisional application No. 62/623,180, filed on Jan. 29, 2018.

(51) Int. Cl.
*A61M 15/00* (2006.01)
*A61B 1/00* (2006.01)
(Continued)

(52) U.S. Cl.
CPC ..... *A61M 25/0054* (2013.01); *A61B 1/00071* (2013.01); *A61L 29/02* (2013.01);
(Continued)

(58) Field of Classification Search
CPC ...... A61B 1/00071; A61B 2017/00309; A61B 2017/00526; A61L 29/02;
(Continued)

(56) References Cited

U.S. PATENT DOCUMENTS 8,292,827 B2 10/2012 Musbach et al.
2003/0069522 A1 4/2003 Jacobsen et al.
(Continued)

FOREIGN PATENT DOCUMENTS

JP 2005-534407 A 11/2005
JP 2007521877 A 8/2007
(Continued)

OTHER PUBLICATIONS

USPTO as International Searching Authority, "International Search Report and Written Opinion," International Application No. PCT/US2019/015741, dated Apr. 30, 2019.
(Continued)

*Primary Examiner* — Tasnim Mehjabin Ahmed
(74) *Attorney, Agent, or Firm* — DENTONS Durham Jones Pinegar

(57) ABSTRACT

An elongated medical device includes an elongated tubular element with a series of flexibility enhancing features along a length of the elongated tubular element. Each flexibility enhancing feature may include a circumferential series of cuts. The cuts of one flexibility enhancing feature may be offset relative to the cuts of a longitudinally adjacent flexibility enhancing feature. The flexibility enhancing features may be grouped into two or more interleaved sets, with each set of circumferential cuts being offset relative to the next set of circumferential cuts. Methods for manufacturing such elongated medical devices are also disclosed.

22 Claims, 2 Drawing Sheets

(51) Int. Cl.
  *A61B 17/00* (2006.01)
  *A61L 29/02* (2006.01)
  *A61M 25/00* (2006.01)

(52) U.S. Cl.
  CPC .............. *A61M 25/0051* (2013.01); *A61B 2017/00309* (2013.01); *A61M 25/0013* (2013.01); *A61M 2025/0042* (2013.01); *A61M 25/0053* (2013.01); *A61M 2205/0266* (2013.01)

(58) Field of Classification Search
  CPC .. A61M 2025/0042; A61M 2205/0266; A61M 25/0013; A61M 25/0051; A61M 25/0053; A61M 25/0054
  See application file for complete search history.

(56) References Cited

U.S. PATENT DOCUMENTS

| | | |
|---|---|---|
| 2005/0177132 A1 | 8/2005 | Lentz et al. |
| 2008/0097398 A1 | 4/2008 | Mitelberg et al. |
| 2009/0062602 A1* | 3/2009 | Rosenberg ........ A61M 25/0147 600/101 |
| 2012/0143175 A1 | 6/2012 | Hermann et al. |
| 2013/0296718 A1* | 11/2013 | Ranganathan ........ A61M 25/09 600/481 |
| 2014/0052097 A1 | 2/2014 | Petersen et al. |
| 2018/0093070 A1 | 4/2018 | Cottone |

FOREIGN PATENT DOCUMENTS

| | | |
|---|---|---|
| JP | 2009519103 A | 5/2009 |
| WO | 9911313 A1 | 3/1999 |

OTHER PUBLICATIONS

Japan Patent Office, "Office Action," Japanese Patent Application No. 2020-562101, Jul. 21, 2022.
Japan Patent Office, "Office Action," Japanese Patent Application No. 2020-562101, Aug. 25, 2021.
European Patent Office, "extended European search report," European Application No. 19744416.9, Oct. 22, 2021.
Japan Patent Office, "Office Action," Japanese Patent Application No. 2022-185637, Oct. 16, 2023.

* cited by examiner

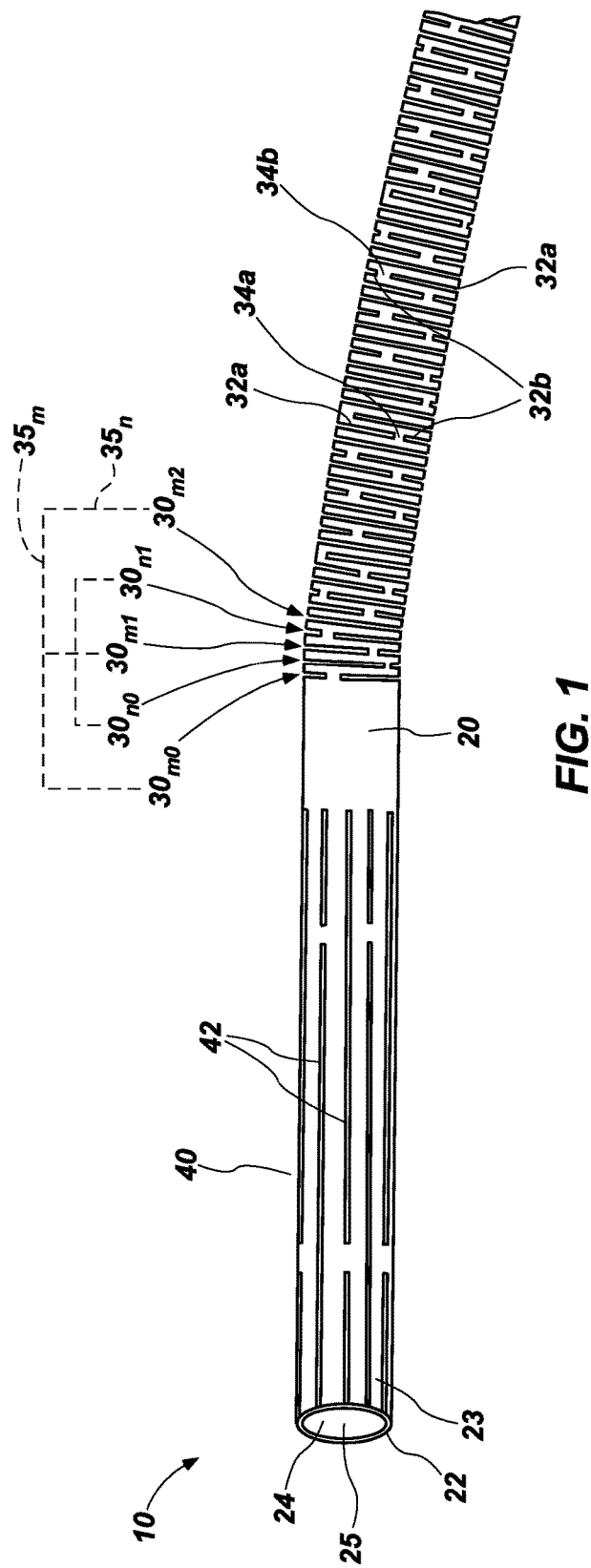
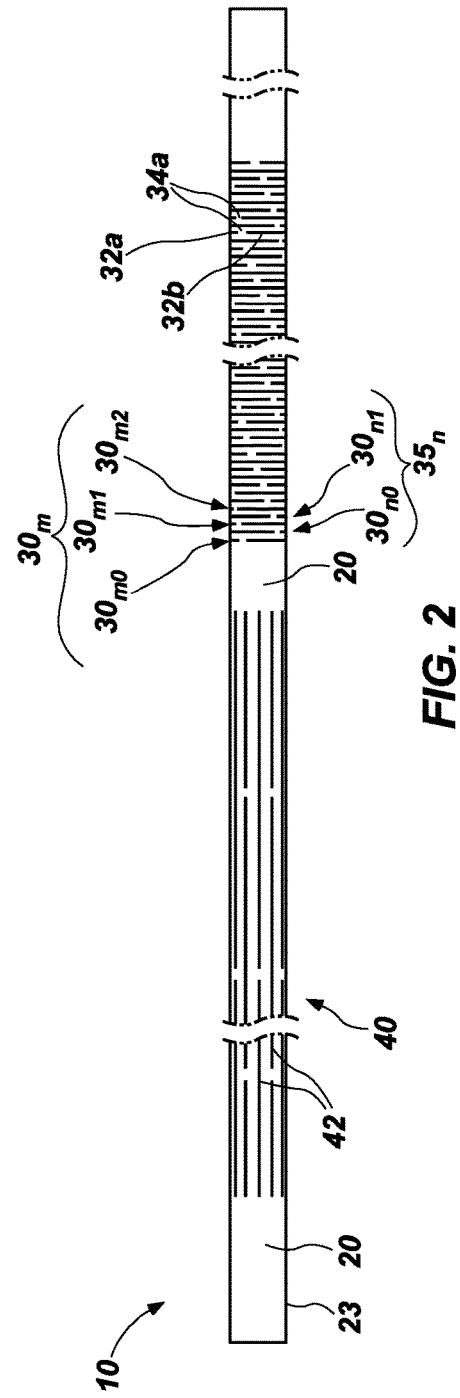

ELONGATED MEDICAL INSTRUMENTS WITH FLEXIBILITY ENHANCING FEATURES

CROSS-REFERENCE TO RELATED APPLICATION

A claim for the benefit of priority to the Jan. 29, 2018 filing date of U.S. Provisional Patent Application No. 62/623,180, titled ELONGATED MEDICAL INSTRUMENTS WITH FLEXIBILITY-ENHANCING FEATURES ("the '180 Provisional Application"), is hereby made pursuant to 35 U.S.C. § 119(e). The entire disclosure of the '180 Provisional Application is hereby incorporated herein.

TECHNICAL FIELD

This disclosure relates generally to elongated medical devices with features that enhance flexibility at one or more locations along the lengths of such elongated medical devices and to arrangements of flexibility-enhancing features along the lengths of elongated medical instruments. Some embodiments according to this disclosure relate to flexibility-enhancing features for hypotubes and to hypotubes that include the flexibility-enhancing features.

RELATED ART

Hypodermic tubes, or "hypotubes," are useful for a variety of purposes. In the medical device industry, hypotubes may facilitate the introduction of catheters through a patient's anatomy. Hypotubes may be manufactured in a variety of lengths and with outer diameters ranging from about 0.120 inch (11 gauge) to 0.005 inch (36 gauge).

Medical hypotubes are commonly formed from stainless steel (e.g., 304 stainless steel, 316 stainless steel, etc.). Stainless steel hypotubes may enhance the ability of a catheter to glide (e.g., push, track, and torque) through a subject's anatomy, but are known for their tendency to kink, particularly when forced through tortuous paths. Nitinol has also been used to form hypotubes. While nitinol hypotubes are kink-resistant, they are much more expensive to manufacture (particularly in developmental stages and in small quantities) than stainless steel hypotubes.

DISCLOSURE

An elongated medical device according to this disclosure includes an elongated tubular element with a series of flexibility enhancing features along a length of the elongated tubular element, which may be referred to as a "longitudinal series" of flexibility enhancing features.

The elongated tubular element may comprise any suitable type of elongated tubular element, including elongated tubular elements that could benefit from enhanced flexibility. In some embodiments, the elongated tubular element may comprise a hypotube. The hypotube may be formed from any suitable material, such as stainless steel (e.g., 304 stainless steel, 316 stainless steel, etc.). A stainless steel hypotube that includes flexibility-enhancing features, such as a series of adjacent cuts that extend around a portion of a circumference of the hyptotube, as disclosed herein, could be less likely to kink than a conventional stainless steel hypotube. A hypotube according to this disclosure could also be formed from any of a variety of other metal alloys, including, but not limited to, nickel-titanium alloys, such as so-called "nitinol" (nickel-titanium Naval Ordinance Laboratory) phase change alloys. In other embodiments, the elongated tubular element of an elongated medical device according to this disclosure could be formed from a polymer. Regardless of the material from which the elongated tubular element is formed, it includes a wall that defines an outer surface of the tubular element and a lumen that extends through at least a portion of a length of the tubular element.

The longitudinal series of flexibility enhancing features are configured and arranged in a manner that enhances a flexibility of the elongated tubular element. Each flexibility enhancing feature may comprise a series of cuts (i.e., a plurality, or two or more, cuts) arranged around a portion of a circumferential location around the elongated tubular element, normal to a longitudinal axis of the elongated tubular element; such a series of cuts may be referred to as a "circumferential series" of cuts and as "circumferentially aligned cuts." In various embodiments, each flexibility enhancing feature may include a circumferential series of two cuts, three cuts, four cuts, etc. Collectively, the circumferential series of cuts that defines such a flexibility enhancing feature may extend around a majority of the circumference of the elongated tubular element (but not completely around the circumference, as such an arrangement would sever the elongated tubular element) while enabling the elongated tubular element to retain sufficient structural integrity to facilitate its intended use as an elongated medical instrument or as part of an elongated medical instrument.

The arc lengths of the cuts that define each circumferential series of cuts of such a flexibility enhancing feature may be the same as one another. The solid regions of the elongated tubular element that alternate with the cuts of a circumferential series of cuts of a flexibility enhancing feature, or the circumferential distance or arc length of each solid region between adjacent, circumferentially aligned cuts, may also have the same lengths. As alternatives, the arc lengths of adjacent, circumferentially aligned cuts of a particular flexibility enhancing feature may differ from one another and/or the arc lengths of the solid regions between the adjacent, circumferentially aligned cuts may differ from one another.

The cuts of one flexibility enhancing feature may be offset relative to the cuts of a longitudinally adjacent flexibility enhancing feature. Such a rotational offset, or circumferential offset, may be fixed and follow a defined pattern. The flexibility enhancing features may be grouped into two or more interleaved sets, with each set of circumferential cuts being offset relative to the next set of circumferential cuts. In some embodiments, every $n^{th}$ (e.g., $2^{nd}$, $3^{rd}$, $4^{th}$, $5^{th}$, etc.) flexibility enhancing feature of a group (e.g., $n_1$, $n_2$, $n_3$, etc.) may be rotationally offset relative to its preceding flexibility enhancing feature of the group (e.g., $n_0$, $n_1$, $n_2$, etc.) by a first, fixed rotational offset. Without limitation, a first set of flexibility enhancing features of a series of flexibility enhancing features may include every odd numbered flexibility enhancing feature of the series, while a second set of flexibility enhancing features of the series of adjacent flexibility enhancing features may include every even numbered flexibility enhancing feature of the series.

The cuts of each flexibility enhancing feature may be rotationally offset from the cuts of its immediately preceding flexibility enhancing feature by a second rotational offset that differs from the first rotational offset; thus, each set of flexibility enhancing features in series along the length of the elongated tubular element may be rotationally offset relative to every other set of flexibility enhancing features by the second rotational offset. In some embodiments, the first rotational offset of one set of flexibility enhancing features (i.e., every $n^{th}$ flexibility enhancing feature; e.g., where n=3, the $1^{st}$, $4^{th}$, $7^{th}$, etc., flexibility enhancing features) may be different from the first rotational offset of a different set of flexibility enhancing features (i.e., every $n^{th}+1$ flexibility enhancing feature; e.g., where n=3, the $2^{nd}$, $5^{th}$, $8^{th}$, etc., flexibility enhancing features; every $n^{th}+2$ flexibility enhancing feature; e.g., where n=3, the $3^{rd}$, $6^{th}$, $9^{th}$, etc., flexibility enhancing features; etc.).

Elongated medical devices with flexibility enhancing features that are offset quasi-randomly or randomly, or that appear to have random rotational offsets relative to one another, are also within the scope of this disclosure.

Methods for defining flexibility enhancing features in an elongated tubular element are also disclosed. Such a method may employ laser cutting techniques, in which an elongated tubular element is introduced into a laser cutting device and moved longitudinally through the laser cutting device. More specifically, a drive element, or a so-called "chuck," may engage the elongated tubular element along a portion of its length and may move the elongated tubular element through the laser cutting device. Movement of the elongated tubular element through the laser cutting device may be incremental. At each increment, a circumferential series of cuts may be made around a particular circumference of the elongated tubular element that is in line with a laser of the laser cutting device; for example, the circumferential series of cuts may be made by rotating the elongated tubular element, etc.

In some embodiments, as the drive element of the laser cutting device reaches a final position along the distance it can travel through the laser cutting device, or its "length of travel" or "throw length," the arc length of the final cut that is made before the drive element disengages the elongated tubular element, returns to its initial position along its length of travel, and re-engages the elongated tubular element may be reduced relative to the lengths of the arcs of the other cuts in the same circumferential series and of other flexibility enhancing features that are defined while the drive element travels from its initial position to its final position within the laser cutting device. The reduction in length of that cut may result in a corresponding decrease in the amount of time required to define a longitudinal series of flexibility enhancing features in the elongated tubular element. In some embodiments, this technique has been shown to reduce laser cutting time by as much as 40% with no measurable impact on the flexibility of the resulting elongated medical device.

Other aspects of the disclosed subject matter, as well as features and advantages of various aspects of the disclosed subject matter, should become apparent to one of ordinary skill in the art through consideration of the ensuing description, the accompanying drawings, and the appended claims.

BRIEF DESCRIPTION OF THE DRAWINGS

In the drawings:

FIG. 1 is a perspective view of a portion of an embodiment of an elongated medical device according to this disclosure;

FIG. 2 is an engineering drawing of a portion of an embodiment of an elongated medical device according to this disclosure;

DETAILED DESCRIPTION

Figure 3:
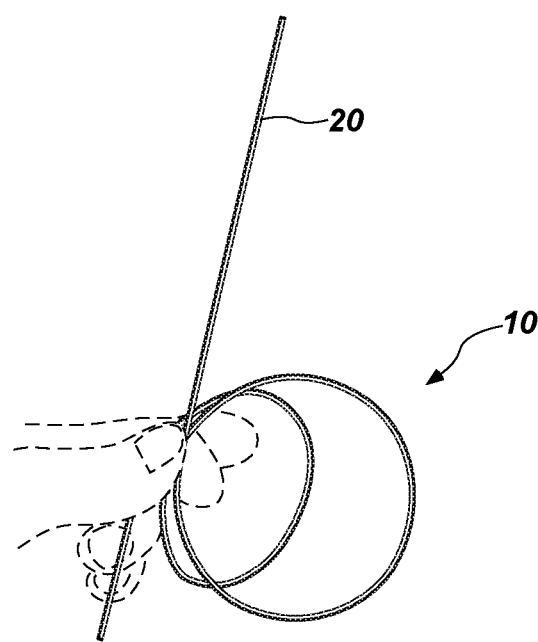
FIG. 3 illustrates the flexibility of an embodiment of an elongated medical device according to this disclosure.

With reference to FIGS. 1 and 2, embodiments of an elongated medical device according to this disclosure are depicted, with FIG. 1 providing a partial perspective view of a portion of the elongated medical device 10 in a curved configuration or a bent configuration and FIG. 2 providing an engineering drawing of a portion of the elongated medical device 10 in a straight configuration. As illustrated, the elongated medical device 10 includes an elongated tubular element 20, a plurality of flexibility enhancing features 30 arranged along a length of the elongated tubular element 20, as well as other optional features.

The elongated tubular element 20 is defined by a wall 22, which is elongated and tubular in shape. The wall 22 includes an outer surface 23 and an inner surface 24 opposite from the outer surface 23. The outer surface 23 of the wall 22 defines an exterior of the elongated tubular element 20, as well as an exterior of the elongated medical device 10 of which the elongated tubular element 20 is a part. The inner surface 24 of the wall 22 defines a lumen 25 that extends through at least a portion of a length of the elongated tubular element 20 and, optionally, of the elongated medical device 10 of which the elongated tubular element 20 is a part. In some embodiments, the lumen 25 may extend through an entire length of the elongated tubular element 20 and, optionally, of the elongated medical device 10 of which the elongated tubular element 20 is a part.

A thickness of the wall 22 of the elongated tubular element 20 may, along with a material from which the elongated tubular element 20 is formed and other dimensions of the elongated tubular element 20 (e.g., its outer diameter (OD), its inner diameter (ID), etc.), impart the elongated tubular element 20 with sufficient structural integrity to enable the lumen 25 of the elongated tubular element 20 to remain open and even substantially retain its cross-sectional (taken normal to the longitudinal axis through the center of the lumen 25) shape (e.g., circularity, etc.) during use of the elongated medical device 10. Additionally, the thickness of the wall 22 may prevent kinking of the elongated tubular element 20 and collapsing of the lumen 25 during use of the elongated medical device 10 (e.g., as the elongated medical device 10 flexes, or curves, along its length, etc.). Thus, the wall 22 may have a thickness that prevents any disruption in the flow of fluids (e.g., liquids, gases, etc.) through the lumen 25 of the elongated tubular element 20 during use of an elongated medical device 10 of which the elongated tubular element 20 is a part. In various embodiments, the wall 22 of the elongated tubular element 20 may have a thickness (i.e., a distance along a radius of the elongated tubular element 20) of about 0.0015 inch (about 38 μm) to about 0.006 inch (about 150 μm).

In addition to the thickness of its wall 22, the OD and ID of the elongated tubular element 20 may have any suitable measurements. As examples, the ID of the elongated tubular element 20, or the diameter of the lumen 25 of the elongated tubular element 20, may be about 0.002 inch (about 50 μm) to about 0.070 inch (about 1.8 mm); the OD of the elongated tubular element 20 may be about 0.005 inch (about 125 μm) to about 0.080 inch (about 2 mm).

The elongated tubular element 20 may, in some embodiments, comprise a hypotube, which may be formed from a suitable metal or metal alloy. Examples of such materials include, but are not limited to, stainless steel (e.g., 304 stainless steel, 316 stainless steel, etc.) and nickel-titanium alloys, including nickel-titanium alloys whose flexibility varies depending upon their temperature (e.g., flexible at ambient temperature, rigid at elevated temperature (e.g., body temperature, etc.); etc.). Alternatively, the elongated tubular element 20 may be formed from a polymer.

With continued reference to FIGS. 1 and 2, each flexibility enhancing feature 30 of an elongated medical device 10 according to this disclosure may comprise cuts 32a, 32b, etc., which may also be individually referred to herein as a "cut 32" and collectively referred to herein as "cuts 32." Each cut 32 may extend from the outer surface 23 of the wall 21 of the elongated tubular element 20 toward the inner surface 24 of the wall 22 of the elongated tubular element 20. The cuts 32 may extend partially through a thickness of the wall 22 or completely through the thickness of the wall 22.

Each flexibility enhancing feature 30 may comprise a circumferential series of cuts 32a, 32b, etc., (i.e., a plurality, or two or more, cuts 32). In various embodiments, each flexibility enhancing feature 30 may include a circumferential series of two cuts 32, three cuts 32, four cuts 32, etc. Collectively, the circumferential series of cuts 32a, 32b, etc., that defines such a flexibility enhancing feature 30 may extend around a majority of the circumference of the elongated tubular element 20, with gaps, or solid regions 34a, 34b, etc., of the elongated tubular element 40, being located between adjacent cuts 32a and 32b, etc., of a circumferential series of cuts 32. Each solid region 34a, 34b, etc., may also be individually referred to herein as a "solid region 34," and solid regions 34a, 34b, etc., may be collectively referred to herein as "solid regions 34." In some embodiments, the cuts 32a, 32b, etc., that define a flexibility enhancing feature 30 may collectively extend around about 75% or more of the circumference of the elongated tubular element 20, with solid regions 34a, 34b, etc., of the elongated tubular element 20 defining about 25% or less of that particular circumference around the elongated tubular element 20. As another option, the circumferential series of cuts 32a, 32b, etc., of a flexibility enhancing feature 30 may extend around about 80% or more of the circumference of the elongated tubular element 20, with solid regions 34a, 34b, etc., of the elongated tubular element 20 defining about 20% or less of that particular circumference around the elongated tubular element 20. Alternatively, the circumferential series of cuts 32a, 32b, etc., of a flexibility enhancing feature 30 may extend around about 90% or more of the circumference of the elongated tubular element 20, with solid regions 34a, 34b, etc., of the elongated tubular element 20 defining about 10% or less of that particular circumference around the elongated tubular element 20. In other embodiments, the circumferential series of cuts 32a, 32b, etc., of a flexibility enhancing feature 30 may extend around about 95% or more of the circumference of the elongated tubular element 20, with solid regions 34a, 34b, etc., of the elongated tubular element 20 defining about 5% or less of that particular circumference around the elongated tubular element 20. In still other embodiments, the circumferential series of cuts 32a, 32b, etc., of a flexibility enhancing feature 30 may extend around about 98% or more of the circumference of the elongated tubular element 20, with solid regions 34a, 34b, etc., of the elongated tubular element 20 defining about 2% or less of that particular circumference around the elongated tubular element 20. As another option, the circumferential series of cuts 32a, 32b, etc., of a flexibility enhancing feature 30 may extend around about 99% or more of the circumference of the elongated tubular element 20, with solid regions of the elongated tubular element 20 defining about 1% or less of that particular circumference around the elongated tubular element 20. Ranges of cut regions and solid regions between any of the foregoing values are also within the scope of this disclosure.

The arc lengths of the cuts 32a, 32b, etc., that define each circumferential series of cuts of a flexibility enhancing feature 30 may be the same as one another. As an example, each flexibility enhancing feature 30 may include a pair of circumferentially aligned cuts 32a and 32b. The circumferentially aligned cuts 32a and 32b of each pair may define diametrically opposed arcs around the circumference of the elongated tubular element 20. The arc defined by each cut 32a, 32b of a pair is less than 180° around the circumference of the elongated tubular element 20 (i.e., the pair of circumferentially aligned cuts 32a and 32b does not extend completely around the circumference of the elongated tubular element). The arc of each cut 32a, 32b of such a pair may extend at least 90°, at least 112.5°, at least 135°, at least 157.5°, at least 165°, about 170°, or at least 172.5° around the circumference of the elongated tubular element 20.

The solid regions 34a, 34b, etc., of the elongated tubular element 20 that alternate with the cuts 32a, 32b, etc., of a circumferential series of cuts 32 of a flexibility enhancing feature 30, or the circumferential distance or arc length of each solid region 34a, 34b, etc., between circumferentially adjacent cuts 32a, 32b, etc., may also have the same arcs or lengths as one another. In the embodiments described in the preceding paragraph, the solid regions 34a and 34b between circumferentially aligned cuts 32a and 32b may also define diametrically opposed arcs around the circumference of the elongated tubular element 20. Respectively, the arc of each solid region 34a, 34b between circumferentially aligned cuts 32a and 32b that extend at least 90° around the circumference may be less than 90°; the arc of each solid region 34a, 34b between circumferentially aligned cuts 32a and 32b that extend at least 112.5° around the circumference may be less than 67.5°; the arc of each solid region 34a, 34b between circumferentially aligned cuts 32a and 32b that extend at least 135° around the circumference may be less than 45°; the arc of each solid region 34a, 34b between circumferentially aligned cuts 32a and 32b that extend at least 157.5° around the circumference may be less than 22.5°; the arc of each solid region 34a, 34b between circumferentially aligned cuts 32a and 32b that extend at least 165° around the circumference may be less than 15°; the arc of each solid region 34a, 34b between circumferentially aligned cuts 32a and 32b that extend about 170° around the circumference may be about 10°; and the arc of each solid region 34a, 34b between circumferentially aligned cuts 32a and 32b that extend at least 172.5° around the circumference may be less than 7.5°.

As alternatives, the arcs and arc lengths of circumferentially adjacent cuts 32a, 32b, etc., of a particular flexibility enhancing feature 30 may differ from one another and/or the arc lengths of the solid regions 34a, 34b, etc., between the circumferentially adjacent cuts 32a, 32b, etc., may differ from one another.

The cuts 32 of one flexibility enhancing feature 30 may be offset relative to the cuts 32 of a longitudinally adjacent flexibility enhancing feature 30. Such a rotational offset may be fixed and follow a defined pattern along a longitudinal series of the flexibility enhancing features of an elongated tubular element 20. In some embodiments, adjacent flexibility enhancing features 30 of a series of flexibility enhancing features 30 may be grouped into two or more interleaved sets, with each set $35_n$, of flexibility enhancing features 30 being offset relative to the next set $35_n$ of flexibility enhancing features 30. Without limitation, as depicted by FIGS. 1 and 2, a first set $35_n$, of flexibility enhancing features 30 of a series of adjacent flexibility enhancing features 30 may include every odd numbered flexibility enhancing feature 30 of the series, while a second set $35_n$ of flexibility enhancing features 30 of the series of adjacent flexibility enhancing features 30 may include every even numbered flexibility enhancing feature 30 of the series. Stated another way, the cuts 32 of every $n^{th}$ (e.g., $2^{nd}$, $3^{rd}$, $4^{th}$, $5^{th}$, etc.) flexibility enhancing feature $30_{n1}$, $30_{n2}$, etc., of a set $35_n$ may be rotationally offset relative to the preceding flexibility enhancing feature $30_{n0}$, $30_{n1}$, etc., of set $35_n$ by a first, fixed rotational offset.

The amount of the first rotational offset, or the rotational offset between adjacent flexibility enhancing features 30 in the series of flexibility enhancing features 30 or sequential flexibility enhancing features 30 in a set 35 of flexibility enhancing features 30 that is interleaved with one or more other sets 35 of flexibility enhancing features 30 of the series may be about 90° or less (i.e., a quarter of a turn, or rotation, around the circumference of the elongated tubular element or less). Series of flexibility enhancing features 30 in which two adjacent or sequential flexibility enhancing features 30 have smaller circumferential offsets of 60° or less, 45° or less, or even 30° or less are also within the scope of this disclosure.

In some embodiments, such as that depicted by FIGS. 1 and 2, a series of adjacent circumferential cuts may have two or more sets of circumferential offsets. Stated another way, the cuts 32 of each flexibility enhancing feature 30 (e.g., flexibility enhancing feature $30_{n0}$, etc.) may be rotationally offset from the cuts 32 of its immediately preceding flexibility enhancing feature 30 (e.g., flexibility enhancing feature $30_{m0}$, etc.) by a second rotational offset that differs from the first rotational offset; thus, each set 35 (e.g., set $35_n$, etc.) of flexibility enhancing features 30 in series along the length of the elongated tubular element 20 may be rotationally offset relative every other set 35 (e.g., set $35_m$, etc.) of flexibility enhancing features 30 by the second rotational offset. In some embodiments, the first rotational offset of one set 35 of flexibility enhancing features 30 (i.e., every $n^{th}$ flexibility enhancing feature 30; e.g., where n=3, the $1^{st}$, $4^{th}$, $7^{th}$, etc., flexibility enhancing features 30) may be different from the first rotational offset of a different set 35 of flexibility enhancing features 30 (i.e., every $n^{th}$+1 flexibility enhancing feature 30; e.g., where n=3, the $2^{nd}$, $5^{th}$, $8^{th}$, etc., flexibility enhancing features 30; every $n^{th}$+2 flexibility enhancing feature 30; e.g., where n=3, the $3^{rd}$, $6^{th}$, $9^{th}$, etc., flexibility enhancing features 30; etc.). For example, the sets 35 may be rotationally offset by a rotation of greater than 0° and less than 180° (e.g., by about 90°, by about 120°, by about 150°, etc.).

Each pair of adjacent flexibility enhancing features 30 in a series of flexibility enhancing features 30 may be longitudinally spaced within 0.030 inch of each other, within 0.020 inch of each other, within 0.010 inch of each other, or even within 0.005 inch of each other. The spacing between adjacent flexibility enhancing features 30 may be constant, it may be varied in a pattern, or it may appear to be random (e.g., a different distance between each adjacent pair of flexibility enhancing feature 30, etc.). The longitudinal distance between adjacent flexibility enhancing features 30, or the pitch, of a series of flexibility enhancing features 30 may define the flexibility of a portion of the elongated medical device 10 along with the series of flexibility enhancing features 30 is located. As the width of each cut 32 may determine how closely adjacent flexibility enhancing features 30 may be positioned adjacent to one another (e.g., flexibility enhancing features 30 with thinner cuts 32 may be positioned at a tighter, or higher, pitch, than flexibility enhancing features 30 with wider cuts 32, etc.), the widths of the cuts 32 and, thus, of the flexibility enhancing features 30 they define may also affect the flexibility of the elongated medical device 10.

In some embodiments, the series of adjacent flexibility enhancing features 30 may extend along a length of a substantial portion of the elongated tubular element 20. In other embodiments, one or more series of flexibility enhancing features 30 may be formed in relative small sections along the length of the elongated tubular element 30.

Circumferential cuts through the wall of elongated tubular element that enhance the flexibility of the elongated tubular element or a portion thereof may be used in combination with longitudinal cuts 42 that define a feature 40 at or near a distal end of the elongated tubular element 20. Various embodiments of features that may be defined by longitudinally extending cuts 42 through the wall of the elongated tubular element 20 are disclosed by U.S. patent application Ser. No. 16/174,205, filed on Oct. 29, 2018 and titled EXOSKELETON DEVICE WITH EXPANDABLE SECTION FOR SCORING ("the '205 Application"). The entire disclosure of the '205 Application is hereby incorporated herein.

In a specific embodiment, an elongated medical device 10 according to this disclosure includes an elongated tubular element 20 that comprises a hypotube with a series of flexibility enhancing features 30 that are spaced about 0.010 inch apart from one another, with each cut $32a$, $32b$ of a pair of circumferentially aligned cuts 32 extending about 165° to about 172.5° around a circumference of the hypotube. Every odd numbered (e.g., third, fifth, seventh, etc.) flexibility enhancing feature 30 (e.g., flexibility enhancing feature $30_{m1}$, $30_{m2}$, etc.) is rotationally offset by about 30° from the previous odd numbered (e.g., first, third, fifth, etc.) flexibility enhancing feature 30 (e.g., flexibility enhancing feature $30_{m0}$, $30_{m1}$, etc.). Every even numbered (e.g., fourth, sixth, eighth, etc.) flexibility enhancing feature 30 (e.g., flexibility enhancing feature $30_{n1}$, etc.) is rotationally offset by about 30° from the previous even numbered (e.g., second, fourth, sixth, etc.) flexibility enhancing feature 30 (e.g., flexibility enhancing feature $30_{n0}$, etc.). Thus, the set $35_m$ of odd numbered flexibility enhancing features 30 is rotationally offset from the set $35_n$ of even numbered flexibility enhancing features 30 (e.g., by about 90°). More specifically, the second flexibility enhancing feature $30_{n0}$ may be offset from the first flexibility enhancing feature $30_{m0}$ (at 0°) by about 90° (at about 90°), the third flexibility enhancing feature $30_{m1}$ may be offset from the second flexibility enhancing feature $30_{n1}$ by about −60° (at about 30°), the fourth flexibility enhancing feature $30_{n2}$ may be offset from the third flexibility enhancing features $30_{m2}$ by about 90° (at about 120°), the fifth flexibility enhancing feature 30 may be offset from the fourth flexibility enhancing feature $30_{n2}$ by about −60° (at about 60°), etc.

The flexibility enhancing features 30 of an elongated medical device 10 with an elongated tubular element 20 that comprises a stainless steel hypotube could render the elongated medical device 10 less likely to kink than a similar elongated medical device with conventionally arranged flexibility enhancing features. FIG. 3 illustrates the flexibility of such an embodiment of an elongated medical device 10, which includes flexibility enhancing features 30 (FIGS. 1 and 2) that are configured and arranged as disclosed herein.

Such an elongated medical device 10 may be used as an exoskeleton device around a catheter to enhance a usefulness of the catheter. For example, an elongated medical device 10 may impart a catheter with added rigidity, include features at or near its distal end that enable a balloon catheter (e.g., an angioplasty balloon, etc.) to score inner surfaces of a subject's vasculature or internal organs (e.g., the devices disclosed by the '205 Application), or may include features at or near its distal end that enable a balloon catheter to control delivery (e.g., infusion, etc.) of drugs or other substances to a particular location within a subject's body (e.g., his or her vasculature, internal organs, etc.).

Figure 4:
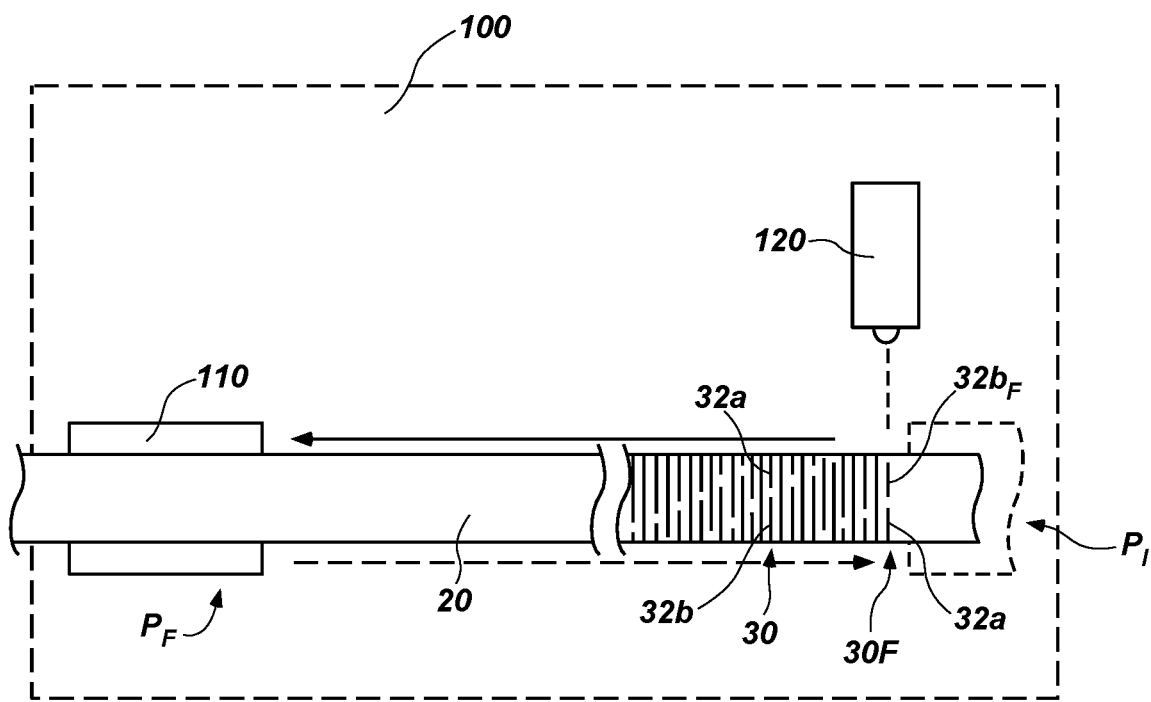
FIG. 4 provides a representation of a method of manufacturing an elongated medical device according to this disclosure.

Referring now to FIG. 4, an embodiment of a method for defining flexibility enhancing features 30 in an elongated tubular element 20 is disclosed. Such a method may employ laser cutting techniques, in which an elongated tubular element 20 is introduced into a laser cutting device 100 and moved longitudinally through the laser cutting device 100. More specifically, a drive element 110, or a so-called "chuck," of the laser cutting device 100 may engage the elongated tubular element 20 along a portion of its length and may move the elongated tubular element 20 through the laser cutting device 100. During each course of travel through the laser cutting device 100, the drive element 110 may move from an initial position $P_1$ to a final position $P_F$. Movement of the elongated tubular element 20 through the laser cutting device 100 may be incremental. The length of each increment may correspond to a distance adjacent flexibility enhancing features 30 are to be spaced apart from one another, or the pitch of the adjacent flexibility enhancing features 30.

A laser 120 of the laser cutting device 100 may generate a laser beam capable of defining a circumferential series of cuts 32a, 32b, etc., that defines each flexibility enhancing feature 30 along the length of the elongated tubular element 20. More specifically, each series of circumferentially aligned cuts 32a, 32b, etc., may be defined at each increment as the drive element 110 carries the elongated tubular element 20 through the laser cutting device 100, at a location, or around a particular circumference, along the length of the elongated tubular element 20 as that location is advanced to a position that is in line with the laser 120. Each circumferential series of cuts 32a, 32b, etc., may be made as the elongated tubular element 20 is rotated within the laser cutting device 100 and/or as the laser 120 moves around the elongated tubular element 20. The width of each cut 32a, 32b, etc., may correspond to the width of the laser beam generated by the laser 120, which width may be adjusted.

As the drive element 110 of the laser cutting device 100 reaches the final position $P_F$ of its travel through the laser cutting device 100, the arc length of the final cut $32b_F$ that is made before the drive element 110 disengages the elongated tubular element 20, returns to its initial position $P_1$ along its length of travel, and re-engages the elongated tubular element 20 may be reduced relative to the lengths of the arcs of the other cuts $32a_F$ in the same circumferential series. As a result, only the final flexibility enhancing feature $30_F$ that is formed with each course of travel of the drive element 110 through the laser cutting device 100 (e.g., one out of hundreds or even thousands of flexibility enhancing features 30 that are defined as the drive element 110 travels along a path that is a few inches long (e.g., 6 inches, 12 inches, etc.); etc.) will include a final cut $32b_F$ that is shorter than its circumferentially aligned cut(s) 32 and than the cuts 32 of the other flexibility enhancing features 30 that were defined during the same course of travel of the drive element 110. Thus, while the proportion in the reduction in length of that cut $32b_F$ may result in a corresponding decrease in the amount of time required to define a longitudinal series of flexibility enhancing features 30 in the elongated tubular element 20, this technique may have no measurable impact on the flexibility of the resulting elongated medical device 10 (FIGS. 1-3).

Although the preceding description and the accompanying drawings are limited to a few specific embodiments, the specific embodiments that have been described and illustrated should not be construed as limiting the scope of any of the appended claims. Features from different embodiments may be employed in combination. All additions to, deletions from, and modifications of the disclosed subject matter that fall within the scopes of the claims are to be embraced by the claims.

What is claimed:

1. An elongated medical device, comprising:
   an elongated tubular element with a wall defining an outer surface and a lumen extending through a length of the elongated tubular element; and
   a flexibility enhancement comprising a series of cuts formed through the wall along at least a portion of a length of the elongated tubular element, each cut of the series of cuts defining an arc around the elongated tubular element of at least 90° but less than 180° and being aligned with another cut, the series of cuts including:
   a first set of cuts, an arc of each first cut of the first set of cuts being offset from an arc of a consecutive first cut of the first set of cuts by a first rotational angle of greater than 0° to about 90°; and
   a second set of cuts, an arc of each second cut of the second set of cuts being offset from an arc of a consecutive second cut of the second set of cuts by a second rotational angle of greater than 0° to about 90°, the second set of cuts being interleaved with the first set of cuts; and
   a final cut at an end of the series of cuts, the final cut having a length that is shorter than a length of every cut of the series of cuts.

2. The elongated medical device of claim 1, wherein the arc of each cut of the series of cuts is at least 112.5° but less than 180°.

3. The elongated medical device of claim 1, wherein the arc of each cut of the series of cuts is at least 135° but less than 180°.

4. The elongated medical device of claim 1, wherein the arc of each cut of the series of cuts is at least 157.5° but less than 180°.

5. The elongated medical device of claim 1, wherein the arc of each cut of the series of cuts is at least 165° but less than 180°.

6. The elongated medical device of claim 1, wherein the arc of each cut of the series of cuts is at least 172.5° but less than 180°.

7. The elongated medical device of claim 1, wherein the first rotational angle is about 30° to about 60°.

8. The elongated medical device of claim 1, wherein longitudinally adjacent cuts of the series of cuts are positioned within about 0.030 inch apart from each other along the length of the elongated tubular element.

9. The elongated medical device of claim 1, wherein longitudinally adjacent cuts of the series of cuts are positioned within about 0.020 inch apart from each other along the length of the elongated tubular element.

10. The elongated medical device of claim 1, wherein longitudinally adjacent cuts of the series of cuts are positioned within about 0.010 inch apart from each other along the length of the elongated tubular element.

11. The elongated medical device of claim 1, wherein the elongated tubular element comprises a hypotube.

12. The elongated medical device of claim 11, wherein the hypotube comprises stainless steel.

13. The elongated medical device of claim 11, wherein the hypotube comprises nitinol.

14. The elongated medical device of claim 1, wherein the elongated tubular element comprises a polymer.

15. An elongated medical device, comprising:
- a hypotube with a wall defining an outer surface and a lumen extending through a length of a tubular element; and
- a series of cuts formed through the wall along a portion of a length of the hypotube, each cut of the series of cuts defining an arc around the hypotube of at least 150° but less than 180° and being aligned with another cut, longitudinally adjacent cuts of the series of cuts being positioned within about 0.020 inch apart from each other along the length of the hypotube, the series of cuts including:
  - a first set of cuts, an arc of each first cut of the first set of cuts being offset from an arc of a consecutive first cut of the first set of cuts by a first rotational angle of about 45° to about 90°; and
  - a second set of cuts, an arc of each second cut of the second set of cuts being offset from an arc of a consecutive second cut of the second set of cuts by a second rotational angle of about 45° to about 90°, the second set of cuts being interleaved with the first set of cuts, each cut of the first set of cuts being offset from a longitudinally adjacent cut of the second set of cuts by a staggered rotational angle that causes a given first cut to be offset from an immediately distally longitudinally adjacent second cut by a rotational angle that differs from a rotational angle the immediately distally longitudinally adjacent second cut is offset from a next immediately distally longitudinally adjacent first cut; and
  - a final cut at an end of the series of cuts and being shorter than every cut of the series of cuts.

16. The elongated medical device of claim 15, wherein the arc of each cut of the series of cuts is at least 165° but less than 180°.

17. The elongated medical device of claim 15, wherein the first rotational angle is about 45° to about 60°.

18. The elongated medical device of claim 15, wherein the first rotational angle is about 45°.

19. The elongated medical device of claim 15, wherein longitudinally adjacent cuts of the series of cuts are positioned within about 0.010 inch apart from each other along the length of the hypotube.

20. The elongated medical device of claim 15, wherein the hypotube comprises stainless steel.

21. The elongated medical device of claim 15, wherein the hypotube comprises nitinol.

22. The elongated medical device of claim 15, wherein the first rotational angle and/or the second rotational angle differs from the staggered rotational angle by about 90° or less.

* * * * *